United States Patent [19]

Winchell et al.

[11] 3,968,221

[45] July 6, 1976

[54] 99M-TECHNETIUM LABELED TIN COLLOID RADIOPHARMACEUTICALS

[75] Inventors: Harry S. Winchell, Lafayette; Morton Barak; Parmer Van Fleet, III, both of Walnut Creek, all of Calif.

[73] Assignee: Medi-Physics, Inc., Emeryville, Calif.

[22] Filed: June 10, 1974

[21] Appl. No.: 477,864

Related U.S. Application Data

[62] Division of Ser. No. 250,738, May 5, 1972, Pat. No. 3,875,299.

[52] U.S. Cl. ........................... 424/1; 206/219; 250/303; 252/301.1 R; 252/313 R; 424/131
[51] Int. Cl.² ................. A61K 43/00; B65D 25/08
[58] Field of Search .................. 424/1, 131; 252/301.1 R, 182, 188.3 R, 313 R; 206/219

[56] References Cited
UNITED STATES PATENTS

| 3,657,003 | 4/1972 | Kenney | 252/313 R X |
| 3,725,295 | 4/1973 | Eckelman et al. | 252/301.1 R |
| 3,767,590 | 10/1973 | Kenney | 252/313 R |
| 3,861,978 | 1/1975 | Connole et al. | 252/313 R X |
| 3,863,004 | 1/1975 | Wolfangel | 252/301.1 R X |

OTHER PUBLICATIONS

Lin et al., Journal of Nuclear Medicine, vol. 13, No. 1, pp. 58–65.

Lin et al., Journal of Nuclear Medicine, vol. 12, No. 5, pp. 204–211.

*Primary Examiner*—Benjamin R. Padgett
*Assistant Examiner*—Christine M. Nucker
*Attorney, Agent, or Firm*—Samuel L. Welt; Bernard S. Leon; R. Hain Swope

[57] ABSTRACT

An improved 99m-technetium labeled tin(II) colloid, size-stabilized for reticuloendothelial organ imaging without the use of macromolecular stabilizers and a packaged tin base reagent and an improved method for making it are disclosed.

3 Claims, No Drawings

99M-TECHNETIUM LABELED TIN COLLOID RADIOPHARMACEUTICALS

RELATED APPLICATIONS

This application is a divisional of U.S. patent application Ser. No. 250,738 filed May 5, 1972 and now U.S. Pat. No. 3,875,299.

BACKGROUND OF THE INVENTION

Most of the radio colloids known in the art require the presence of a stabilizing material, usually a macromolecule, to prevent adherence of the colloid to the walls of its container and agglomeration of the colloid particles into macroaggregates. While gelatin and dextran have been used for this purpose in the past, occasional adverse reactions have been associated with them. The use of human serum albumin as a macromolecular stabilizer for a 99m-technetiumtin(II) colloid the particle size of which was stabilized in a range suitable for reticuloendothelial organ imaging is disclosed in an article entitled "A Simple 'Kit' Method for the Preparation of a Technetium-tin(II) Colloid and a Study of its Properties" by Max S. Lin and H. Saul Winchell in *Journal of Nuclear Medicine* Vol. 13, No. 1, pages 58–65. These macroaggregate stabilizers are essential to such preparations as they will tend to coagulate and settle if the stabilizers are omitted therefrom. In accordance with the present invention it has been found that stable, efficiently labeled technetium-tin (II) colloid having a particle size suitable for reticuloendothelial imaging can be prepared without the use of the macroaggregate stabilizers taught by the prior art.

DETAILED DESCRIPTION OF THE INVENTION

This invention relates generally to 99m-technetium labeled tin(II) colloids useful for scintigraphic imaging of reticuloendothelial organs and more particularly relates to improved 99m-technetium labeled tin(II) colloids which are size-stabilized for liver, spleen and bone marrow scintigraphy without the use of macromolecular stabilizers. The invention further relates to a packaged tin(II) base reagent for preparing size-stabilized technetium labeled tin colloids and a simple method for using the reagent with generally available 99m-technetiumpertechnetate saline solutions.

In accordance with the present invention, an improved tin(II) reagent is provided which has a particle size requisite for reticuloendothelial organ imaging, is effectively labeled with 99m-technetium and is sufficiently stable so that the use of macromolecular stabilizing materials is not required.

The improved reagent in accordance with the present invention comprises a 1 millimolar colloid of hydrolyzed stannous chloride in pyrogen-free water aseptically enclosed in a nitrogen purged ampule. Such an ampule, preferably containing 2.2 ml. of 1mM̄ hydrolyzed stannous chloride is ready for use and has a substantially unlimited shelf life. The reagent may be prepared by dissolving in sterile, pyrogen-free water (U.S.P.) a tin chloride prepared by reacting metallic tin with hydrochloric acid or by adding anhydrous stannous chloride flakes to pyrogen-free water to achieve a 1mM̄ concentration.

It is essential to the proper functioning of the reagent of the invention that the tin ions be kept in the reduced Sn(II) state. By so doing, the particle size of the labeled tin colloid is stabilized. This stabilization is accomplished by the stringent elimination of oxygen, oxidizing catalysts and trace elements which may function as oxidants or oxidizing catalysts for the tin (II). When the tin (II) solution is prepared, it is sterilized, for example by passage through a 0.22 micron Millipore filter directly into sterile ampules which are subsequently purged with Millipore-filtered nitrogen and aseptically sealed.

In use, the improved reagent of the invention is mixed with 99m-technetium-pertechnetate in normal saline such as that generally eluted from technetium generators, to form an efficiently labeled technetium-tin(II) colloid which is size stabilized for scintigraphic imaging of liver, spleen and bone marrow. The resulting colloid remains stable for a practical time period and does not appreciably aggregate into larger colloid particle sizes which are unsuitable for reticuloendothelial organ studies. No macromolecular stabilizers are required, as in the prior art, to maintain the proper particle size if the colloid is used within about a twentyfour hour period. It, of course, can be stabilized with a macromolecular material for longer term stability.

The size-stabilized technetium labeled tin(II) colloid of the invention is prepared and ready for injection in a simple four-step procedure. In the first step, using an aseptic technique, enough 99m-technetium-pertechnetate in normal saline solution is drawn into a syringe to provide the amount of radioactivity desired for administration to a single patient. This generally is in the order of 2–3 mCi. In a second step, an ampule of the improved tin base reagent described above is opened aseptically and enough reagent is drawn into the same syringe containing the pertechnetate to result in a final proportion of one part by volume of reagent to form one to four parts by volume of pertechnetate solution. In a third step, a small volume of air is drawn into the syringe and the syringe shaken well for about ten seconds to assure complete mixing. Finally, to insure optimum results, the efficiently labeled tin(II) colloid is allowed to incubate at room temperature for from seven to ten minutes after mixing. The preparation is then intravenously injected slowly into the patient.

It has been found that an accumulation of over 85% of the administered 99m-technetium radioactivity in the liver and spleen of rats can be achieved with as little as one part by volume of the improved tin (II) base reagent of the present invention to nineteen parts by volume of 99m-technetium-pertechnetate in saline or as much as seven parts by volume of the base reagent to three parts by volume of 99m-technetium solution. It is preferred for optimum results to utilize one part reagent to from one to four parts technetium-pertechnetate in saline. Although formation of the labeled tin colloid is very rapid, best results are obtained wherein the labeled preparation is allowed to incubate for from seven to ten minutes at room temperature prior to intravenous injection.

In vivo distribution of the improved colloid and radiation dose to various organs are comparable to those associated with other technetium labeled colloids. For 3mCi of administered 99m-technetium this is in order of 0.05 rads total body, 0.04 rads male gonads, 0.07 rads female gonads, 0.72–0.99 rads liver, 0.48–1.3 rads spleen, 0.07–0.10 rads red bone marrow.

The above examples and the described procedures are for illustrative purposes only. It will be apparent to those skilled in the art that both may be modified within the scope of the invention defined in the following claims.

We claim:

1. A packaged reagent for preparing size-stabilized 99m-technetium labeled colloids consisting of a 1 millimolar colloid of hydrolyzed stannous chloride in sterile, pyrogen-free water aseptically enclosed in a nitrogen-purged ampule.

2. The packaged reagent of claim 1 wherein substantially all of the tin ions are in the reduced tin (II) state.

3. A method of preparing a sterile tin (II) base reagent suitable for the preparation of size-stabilized 99m-technetium labeled colloids which comprises:
   a. adding sufficient anhydrous stannous chloride to sterile, pyrogen-free water to form a 1 millimolar colloid;
   b. filling a sterile, sealable ampule package with said colloid;
   c. nitrogen purging said package thereby eliminating oxygen therefrom; and
   d. aseptically sealing said package in an airtight condition.

* * * * *